(12) United States Patent  
Greenberg et al.

(10) Patent No.: US 9,072,888 B2
(45) Date of Patent: *Jul. 7, 2015

(54) VISUAL PROSTHESIS WITH AN IMPROVED ELECTRODE ARRAY ADAPTED FOR FOVEAL STIMULATION

(71) Applicant: Second Sight Medical Products, Inc., San Fernando, CA (US)

(72) Inventors: Robert J Greenberg, Los Angeles, CA (US); Ashish Ahuja, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,218

(22) Filed: Oct. 14, 2013

(65) Prior Publication Data

US 2014/0309710 A1    Oct. 16, 2014

Related U.S. Application Data

(62) Division of application No. 13/295,931, filed on Nov. 14, 2011, now Pat. No. 8,588,921.

(60) Provisional application No. 61/413,271, filed on Nov. 12, 2010.

(51) Int. Cl.
*A61N 1/05* (2006.01)
*A61N 1/36* (2006.01)

(52) U.S. Cl.
CPC .......... *A61N 1/0543* (2013.01); *A61N 1/36046* (2013.01)

(58) Field of Classification Search
None
See application file for complete search history.

(56) References Cited

U.S. PATENT DOCUMENTS

| | | | |
|---|---|---|---|
| 4,573,481 | A | 3/1986 | Bullara |
| 4,628,933 | A | 12/1986 | Michelson |
| 4,837,049 | A | 6/1989 | Byers et al. |
| 5,109,844 | A | 5/1992 | de Juan, Jr. et al. |
| 5,215,088 | A | 6/1993 | Normann et al. |
| 5,935,155 | A | 8/1999 | Humayun et al. |
| 6,400,989 | B1 | 6/2002 | Eckmiller |
| 6,458,157 | B1 | 10/2002 | Suaning |
| 7,149,586 | B2 | 12/2006 | Greenberg et al. |
| 7,177,697 | B2 | 2/2007 | Eckmiller et al. |
| 2009/0326623 | A1 * | 12/2009 | Greenberg et al. ........... 607/116 |

* cited by examiner

*Primary Examiner* — Brian T Gedeon
(74) *Attorney, Agent, or Firm* — Scott B. Dunbar

(57) ABSTRACT

The present invention is an improved method of electrically stimulating percepts in a patient with a visual prosthesis, to induce a more controlled perception of light. In particular, the present invention is an improved electrode array to maximize retinal response. The array of the present invention is an array with a center section with no electrode, surrounded by a ring of small high density electrodes. Electrodes beyond to ring are gradually larger and more widely spaced.

18 Claims, 6 Drawing Sheets

VISUAL PROSTHESIS WITH AN IMPROVED ELECTRODE ARRAY ADAPTED FOR FOVEAL STIMULATION

CROSS REFERENCE TO RELATED APPLICATIONS

This application is a divisional application of U.S. patent application Ser. No. 13/295,931, filed Nov. 14, 2011, for Visual Prosthesis with an Improved Electrode Array Adapted for Foveal Stimulation, which claims benefit of, and incorporates by reference, U.S. Provisional Patent Application 61/413,271, filed Nov. 12, 2010, for Method of Controlling the Temporal Dynamics of Percepts in a Visual Prosthesis. This application is related to an incorporates by reference, U.S. Pat. No. 7,149,585, for Variable Pitch Electrode Array, and U.S. Pat. No. 8,014,878, for Flexible Circuit Electrode Array.

FIELD OF THE INVENTION

The present invention is an improved method of electrically stimulating percepts in a patient with a visual prosthesis, to induce a more controlled perception of light. In particular, the present invention is an improved electrode array to maximize retinal response.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal).

This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

U.S. Pat. No. 7,149,586 to Greenberg teaches an electrode array with variable pitch, smaller electrodes closer together in the center and larger electrodes further apart in the periphery.

U.S. Pat. No. 7,177,697 to Eckmiller discloses retinal electrode array with electrodes grouped to zones, each zone with different pitch.

SUMMARY OF THE INVENTION

The present invention is an improved method of electrically stimulating percepts in a patient with a visual prosthesis, to induce a more controlled perception of light. In particular, the present invention is an improved electrode array to maximize retinal response. The array of the present invention is an array with a center section with no electrode, surrounded by a ring of small high density electrodes. Electrodes beyond to ring are gradually larger and more widely spaced. The array includes a center portion with no electrodes over the foveal pit, a high density of small electrodes surrounding the center portion, which gradually increase in both size and spatial pitch moving away from the fovea.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of t4he invention should be determined with reference to the claims.

Figure 1:
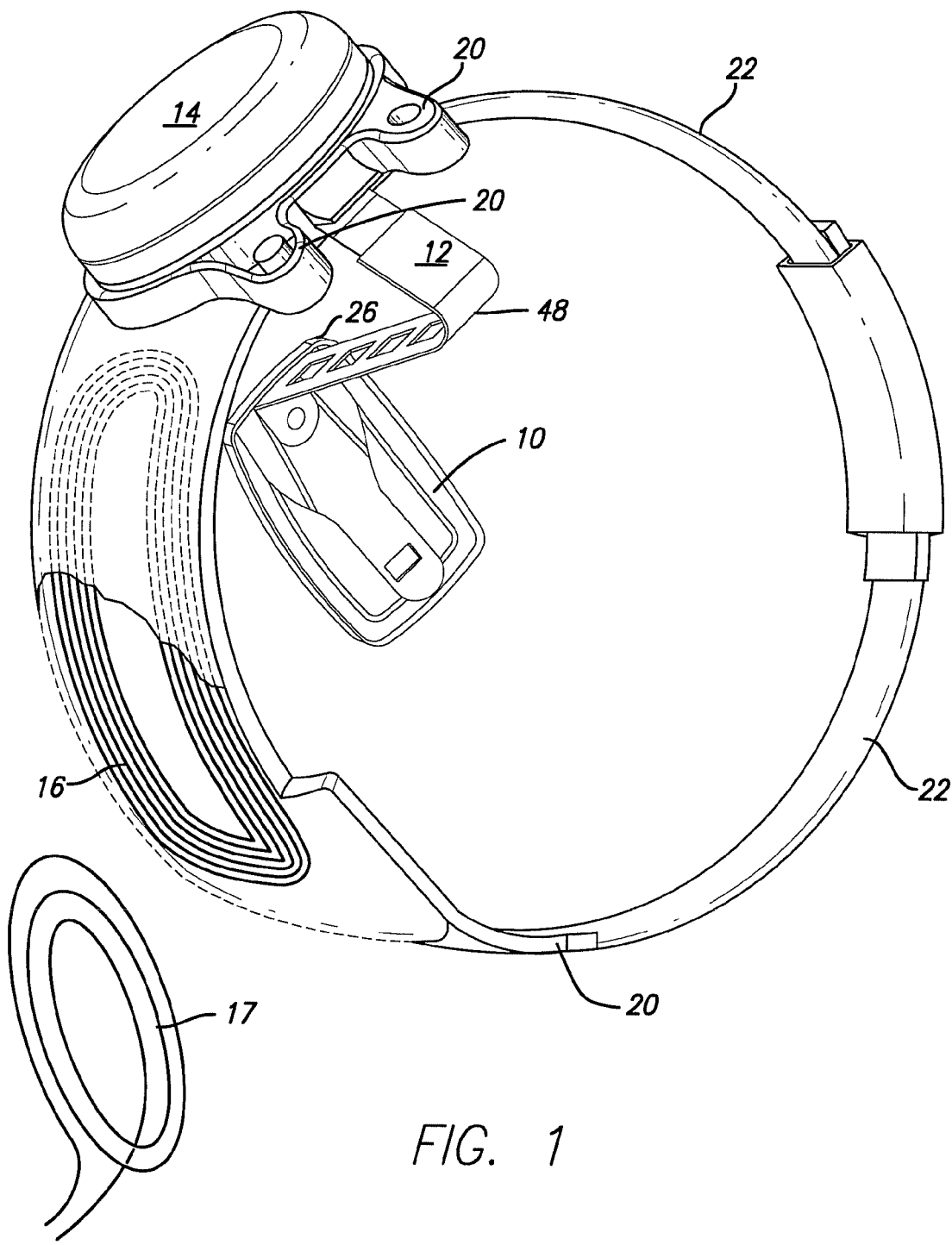
FIG. 1 is a perspective view of the implanted portion of the preferred retinal prosthesis.
Figure 2:
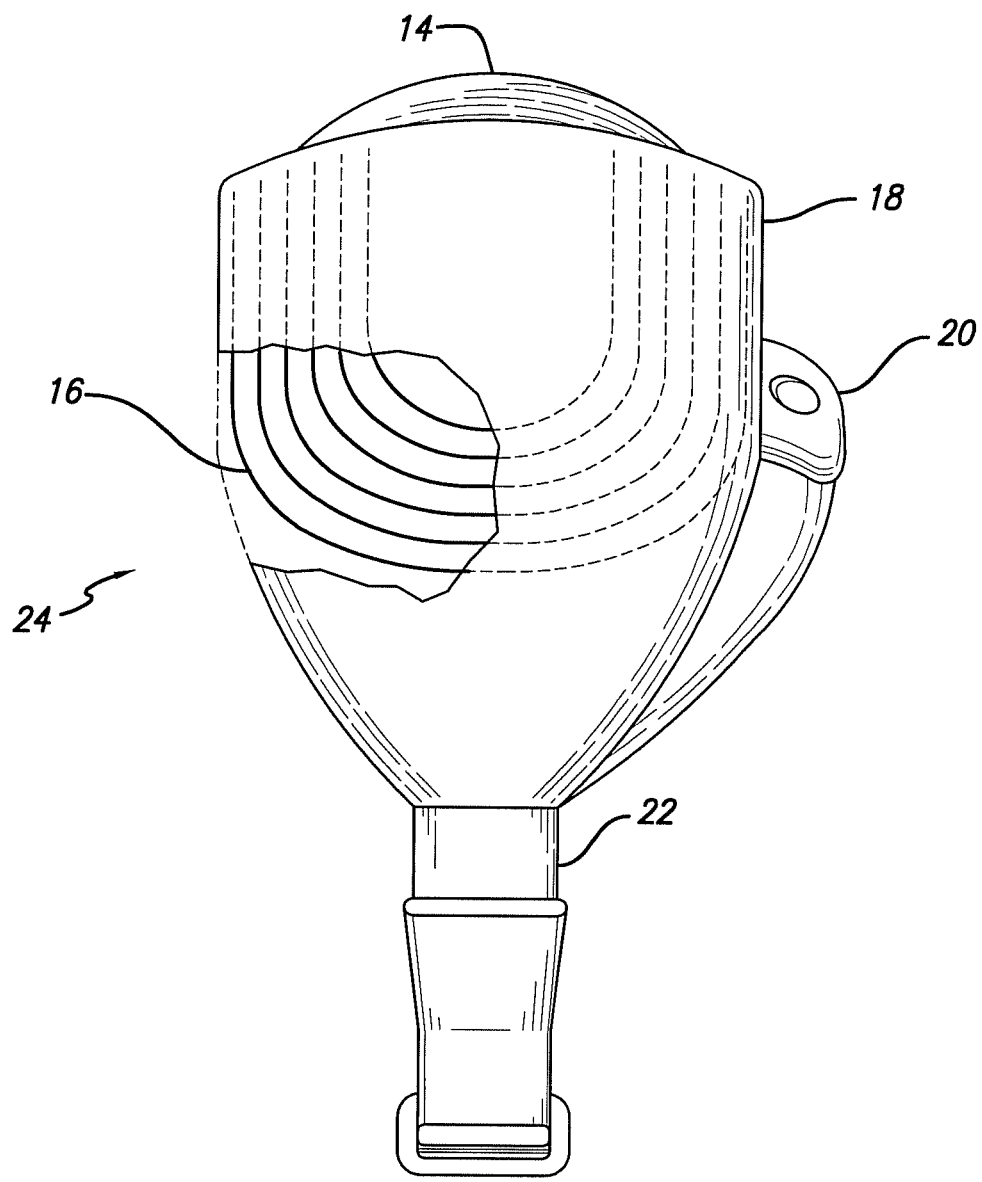
FIG. 2 is a side view of the implanted portion of the preferred retinal prosthesis showing the strap fan tail in more detail.

FIGS. 1 and 2 present the general structure of a visual prosthesis used in implementing the invention.

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the electronics package 14 and secondary inductive coil 16 end to end. The secondary inductive coil 16 is placed around the electronics package 14 in the molded body 18. The molded body 18 holds the secondary inductive coil 16 and electronics package 14 in the end to end orientation and minimizes the thickness or height above the sclera of the entire device. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14. The strap 22 further includes a hook 28 the aids the surgeon in passing the strap under the rectus muscles.

Figure 3:
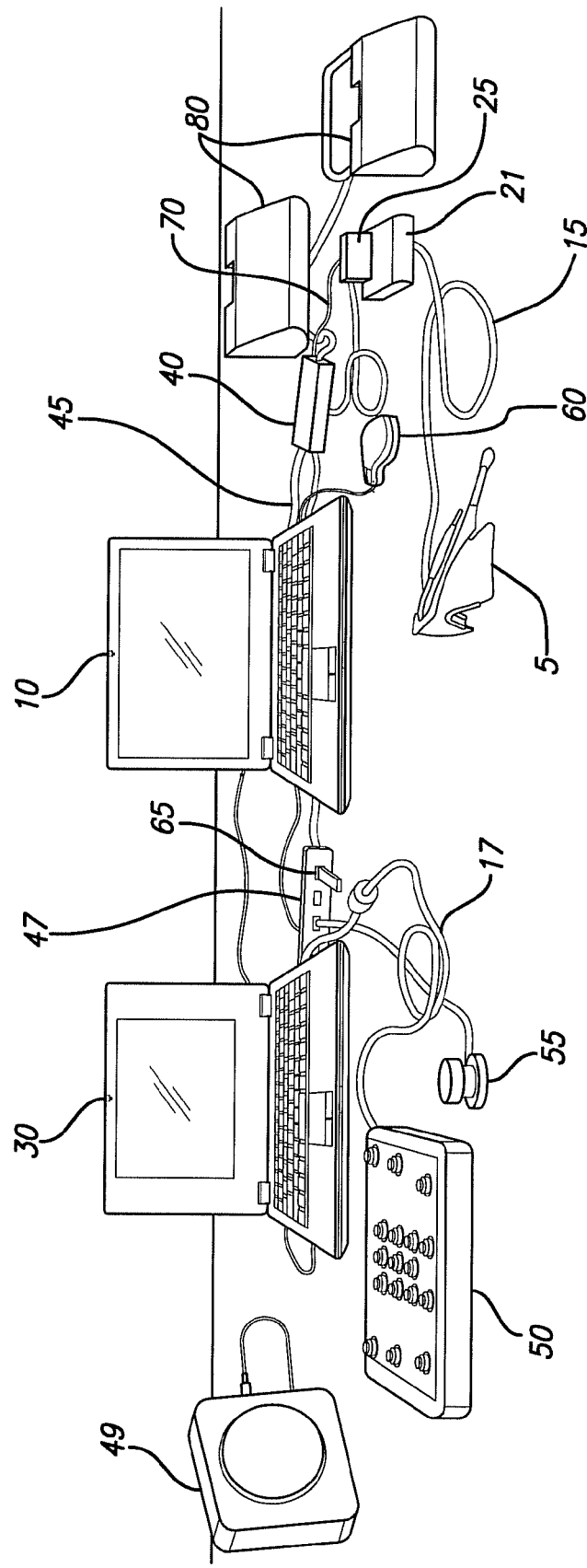
FIG. 3 shows the components of a visual prosthesis fitting system.

Referring to FIG. 3, a Fitting System (FS) may be used to configure and optimize the visual prosthesis (3) of the Retinal Stimulation System (1).

The Fitting System may comprise custom software with a graphical user interface (GUI) running on a dedicated laptop computer (10). Within the Fitting System are modules for performing diagnostic checks of the implant, loading and executing video configuration files, viewing electrode voltage waveforms, and aiding in conducting psychophysical experiments. A video module can be used to download a video configuration file to a Video Processing Unit (VPU) (20) and store it in non-volatile memory to control various aspects of video configuration, e.g. the spatial relationship between the video input and the electrodes. The software can also load a previously used video configuration file from the VPU (20) for adjustment.

The Fitting System can be connected to the Psychophysical Test System (PTS), located for example on a dedicated laptop (30), in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Any time stimulation is sent to the VPU (20), the stimulation parameters are checked to ensure that maximum charge per phase limits, charge balance, and power limitations are met before the test stimuli are sent to the VPU (20) to make certain that stimulation is safe.

Using the psychophysics module, important perceptual parameters such as perceptual threshold, maximum comfort level, and spatial location of percepts may be reliably measured.

Based on these perceptual parameters, the fitting software enables custom configuration of the transformation between video image and spatio-temporal electrode stimulation parameters in an effort to optimize the effectiveness of the retinal prosthesis for each subject.

The Fitting System laptop (10) is connected to the VPU (20) using an optically isolated serial connection adapter (40). Because it is optically isolated, the serial connection adapter (40) assures that no electric leakage current can flow from the Fitting System laptop (10).

As shown in FIG. 3, the following components may be used with the Fitting System according to the present disclosure. A Video Processing Unit (VPU) (20) for the subject being tested, a Charged Battery (25) for VPU (20), Glasses (5), a Fitting System (FS) Laptop (10), a Psychophysical Test System (PTS) Laptop (30), a PTS CD (not shown), a Communication Adapter (CA) (40), a USB Drive (Security) (not shown), a USB Drive (Transfer) (not shown), a USB Drive (Video Settings) (not shown), a Patient Input Device (RF Tablet) (50), a further Patient Input Device (Jog Dial) (55), Glasses Cable (15), CA-VPU Cable (70), CFS-CA Cable (45), CFS-PTS Cable (46), Four (4) Port USB Hub (47), Mouse (60), LED Test Array (80), Archival USB Drive (49), an Isolation Transformer (not shown), adapter cables (not shown), and an External Monitor (not shown).

The external components of the Fitting System according to the present disclosure may be configured as follows. The battery (25) is connected with the VPU (20). The PTS Laptop (30) is connected to FS Laptop (10) using the CFS-PTS Cable (46). The PTS Laptop (30) and FS Laptop (10) are plugged into the Isolation Transformer (not shown) using the Adapter Cables (not shown). The Isolation Transformer is plugged into the wall outlet. The four (4) Port USB Hub (47) is connected to the FS laptop (10) at the USB port. The mouse (60) and the two Patient Input Devices (50) and (55) are connected to four (4) Port USB Hubs (47). The FS laptop (10) is connected to the Communication Adapter (CA) (40) using the CFS-CA Cable (45). The CA (40) is connected to the VPU (20) using the CA-VPU Cable (70). The Glasses (5) are connected to the VPU (20) using the Glasses Cable (15).

Figure 4:
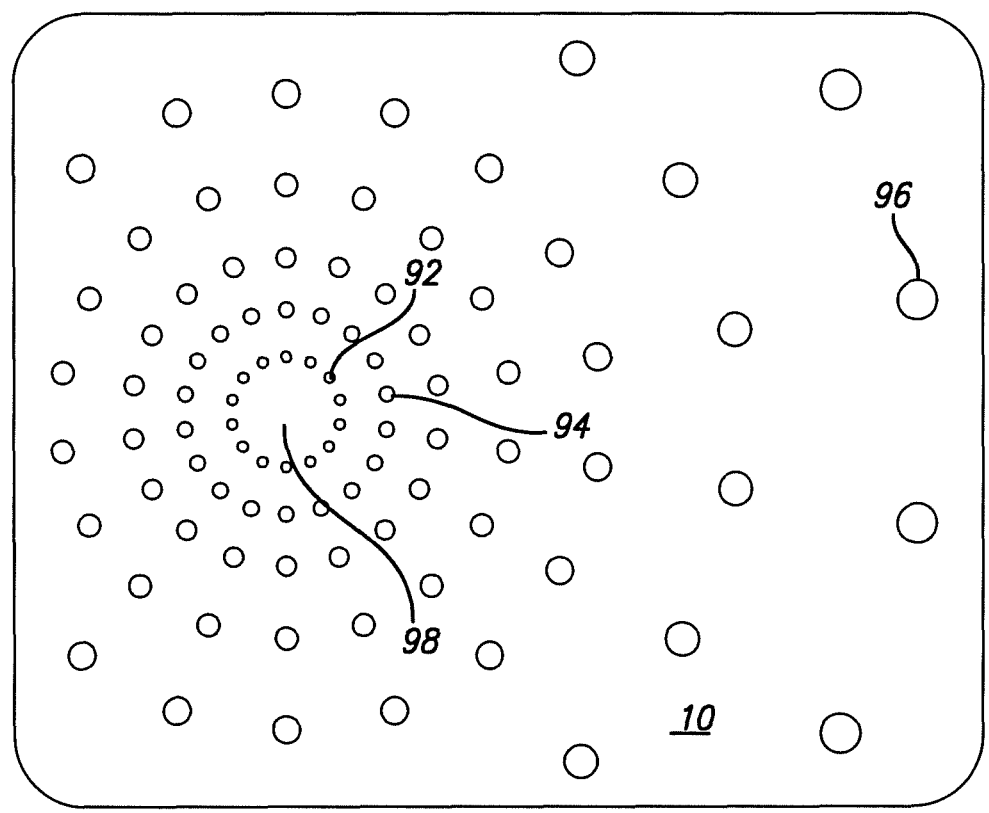
FIG. 4 is a perspective view of the preferred electrode array for retinal stimulation.

The present invention provides an array of variable pitch, variable size electrodes. FIG. 4 shows the invention applied to a retinal stimulator for artificial sight. Electrodes on the preferred retinal electrode array 10 begin very small and close together beyond the center section 98 at the fovea. The electrode array has a center section 98, with no electrodes, possibly a hole in the array. A hole in the array would aid a surgeon in properly placing the array. The center section 98 is placed directly over the fovea and is preferably about 1 mm (millimeter) in radius from the center of the fovea. This area exhibits high thresholds of perception and is generally not worth stimulating. An inner ring of electrodes 92 are the smallest and the closest together and stimulate the portion of the retina with the lowest thresholds. The inner ring of electrodes 98 is preferably about 1.2 mm in radius from the center of the fovea. A subsequent ring of electrodes 94 includes slightly larger electrodes with a slightly larger spatial pitch, as thresholds in this area are slightly higher. The ideal area to stimulate is between 1.2 mm and 3 mm from the center of the fovea. Peripheral electrodes 96 are larger, with a larger spatial pitch, and beyond 3 mm from the center of the fovea.

The inner ring of electrodes 92 are approximately 10 microns in width and are placed 5 microns apart. The size and pitch of the electrodes increases proportionally moving away from the fovea. The preferred electrode array extends further from the fovea in the direction opposite from the optic nerve (not shown), with the largest electrode 96 at the furthest point from the optic nerve. The largest electrode is 1 millimeter in width and 4 millimeters from the nearest electrode. The preferred array body is curved to match the curvature of the retina.

It should be noted that FIG. 4 is not drawn to scale as a scale drawing would be impossible, given PTO accepted dimensions. Further, the preferred electrode array would have far more electrodes than those shown. Several different types of electrode are possible in a retinal electrode array such as spikes, mushrooms or other elongated or recessed shapes. The present invention is independent of the type of electrode used. The variation of electrode size is due to limitations in the charge density supported by current electrode designs. As electrodes are farther from the fovea greater charge is needed, and therefore, larger electrodes are need. Future electrode designs may improve charge density capability obviating the need to vary electrode size. In such a case, it would still be advantageous to vary electrode pitch.

Figure 5:
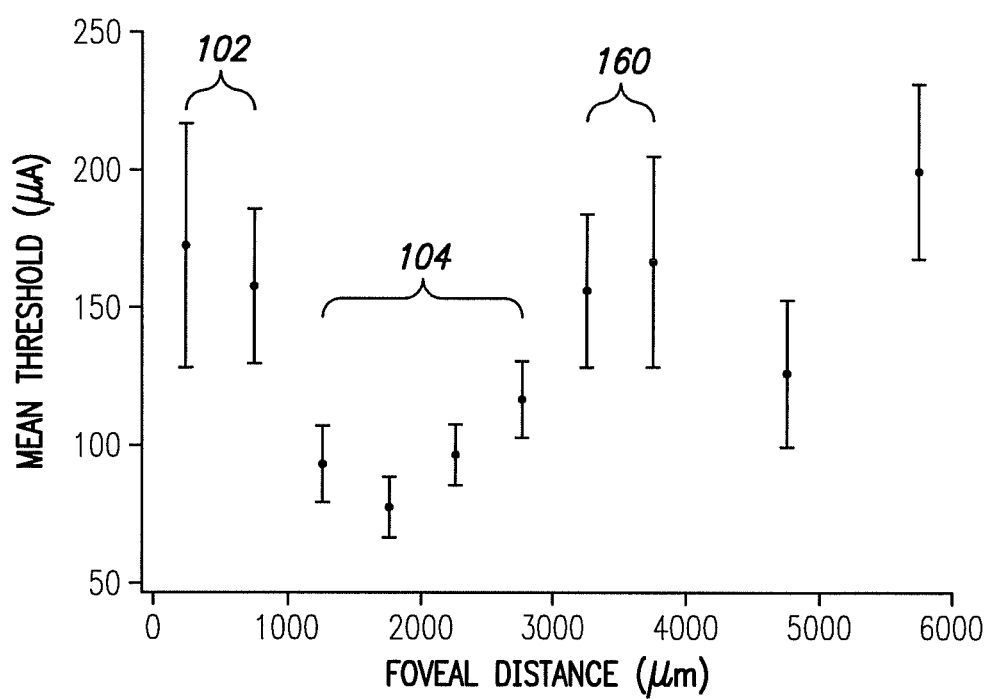
FIG. 5 is a table showing threshold vs. foveal distance.

FIG. 5 shows the results of experiments on human retina. The table shows thresholds in μA (micro amps) versus distance from the center of the fovea in pm (micrometers). A center area 102 within 1 mm of the center of the fovea has higher thresholds. A ring of about 1.2 mm to 3 mm 104 from the center of the fovea has improved thresholds, but thresholds gradually increase with distance from the center of the fovea. The area beyond 3 mm from the center of the fovea 160 again has high thresholds.

In order to determine how many subjects exhibited a significant correlation between threshold and electrode-fovea distance without being affected by the confounding factor of electrode-retina distance, only electrodes in contact with the retina were considered. Electrodes with thresholds below 25 μA had a mean foveal-distance of 1777±121 μm (n=56 electrodes) compared with a mean foveal-distance of 2318±76 μm (n=299 electrodes) for all electrodes with thresholds above 25 μA. Electrodes in contact with thresholds below 50 μA had a mean foveal-distance of 1886±81 μm (n=134 electrodes) compared with a mean foveal-distance of 2439±93 μm (n=216 electrodes) for all electrodes with thresholds above 50 μA. Although electrodes with thresholds below these cutoff amplitudes were on average closer to the fovea compared with all other electrodes in contact with the retina, a non-monotonic relationship between mean threshold and the percentage of electrodes with thresholds below 233 μA was observed when these threshold measures were plotted against foveocentric annular bin. (Bins of electrodes contacting the retina were 500 μm wide; ranged from 11 to 63 electrodes.)

Mean threshold exhibited a broad minimum ranging from 1-2.5 mm away from the fovea, with an absolute minima of 93±14 μA for the 1-1.5 mm range. The percentage of electrodes with thresholds below 233 μA had a maximum of 90.8% (57 of 63 electrodes) in the 1.5-2 μm bin. When testing was performed up to the 677 μA limit 100% of electrodes (n=43) had thresholds in the 0.5-1 mm bin. For all electrodes in contact with the macula (within 3 mm of fovea centralis), 80.9% had thresholds below 233 μA and 90.3% had thresholds below 677 μA.

Single variable regression analysis weighted by electrode count was performed in order to quantify and compare the effects of mean electrode-fovea distance and light threshold (implanted and fellow eyes) on mean electrode threshold, and percentage of available electrodes with thresholds below both the 0.35 mC/cm$^2$ (233 μA) and 1 mC/cm$^2$ (677 μA) charge density limits. Subjects with at least five confirmed electrodes in contact with the retina were included when regressing mean electrode-fovea distance.

Neither mean electrode-fovea distance nor mean geometric electrode-fovea distance correlated with any of the response measures when electrodes at all retinal distances were included ($p>0.2$). Linear regression also showed no significant relationship with measures of threshold when only electrodes in contact with the retina were considered. This is consistent with the fact that both mean threshold and percent of electrodes with thresholds below 233 μA had some local minima or maxima when plotted against binned foveal distance. However, when only electrodes in contact with the retina, and within 3 mm of the fovea were considered there was a strong direct relationship between mean foveal distance and measures of threshold ($R^2 \geq 0.49$; $p<0.01$). In contrast, when only electrodes more than 3 mm from the fovea were considered there was no significant relationship with any measures of threshold ($p>0.1$). Though weaker than these mean measures of retinal and foveal distance, implanted eye light threshold also correlated well with mean electrode threshold ($p<0.01$) and the percentage of electrodes with thresholds below 0.35 mC/cm$^2$ ($<0.05$). Light threshold of the fellow eye did not significantly correlate with any of the response measures, however, the goodness-of-fit and p-values did show the same relative trend as with the implanted eye light thresholds. There was no correlation with age ($p>0.5$; n=7 subjects) or self-reported onset of blindness ($p>0.5$; n=8 subjects).

Figure 6:
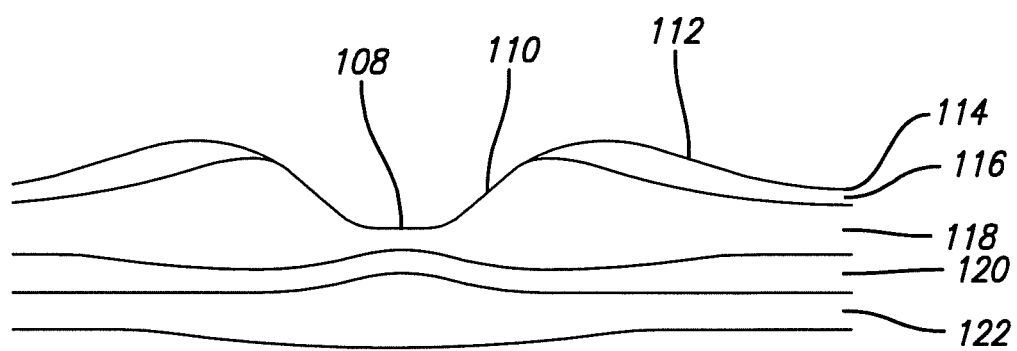
FIG. 6 is a diagram showing how retina physiology relates to the electrode array of the present invention.

FIG. 6 shows how this data relates to retina physiology. The center of the fovea is a pit 108 surrounded by an up slope 110 which is surrounded by a down slope 112. The pit 108 and up slope 110 are about 1 mm in radius. The down slope 112 is between 1.2 mm and 3 mm. It is the down slope that exhibits the lowest thresholds. The retina is made up of layers, the retinal limiting membrane 114, the ganglion cell layer 116, the inner nuclear layer 118, the outer nuclear layer 120 and the rods and cones 122. It should be noted that the down slope 122 has the lowest thresholds and the thickest ganglion layer. The up slope 110 and pit 108 have a highly compressed ganglion cell layer.

In an alternate embodiment of the present invention the center portion is not free of electrodes, but has a few large electrodes (or even a single large electrode) similar to the electrodes in the periphery. The threshold response within the foveal pit is similar to the threshold response in the periphery.

Accordingly, what has been shown is an improved method making a hermetic package for implantation in a body. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. An implantable electrode array for retinal stimulation comprising;
   An array body suitable to be implanted adjacent to a retina near its fovea;
   a ring of high density electrodes 3 millimeters or less from a center point of the array, which contains no electrodes; and
   gradually larger and more widely spaced electrodes beyond 3 millimeters from the center point of the array.

2. The implantable electrode array according to claim 1, wherein spatial pitch intervals are smaller toward the center point of the array body and increasing toward an outer edge of the array body.

3. The implantable electrode array according to claim 1, wherein the electrodes are of varying size.

4. The implantable electrode array according to claim 3, wherein the varying size of the electrodes is small toward the center point of the array body, and increases toward an outer edge of the array body.

5. The implantable electrode array according to claim 1, wherein the varying intervals of the electrodes increases proportionally to a distance from the center point.

6. The implantable electrode array according to claim 4, wherein the varying size of the electrodes increases proportionally to a distance from the center point.

7. The implantable electrode array according to claim 1, wherein the electrodes are elongated electrodes.

8. The implantable electrode array according to claim 7, wherein the elongated electrodes are mushroom shaped electrodes.

9. The implantable electrode array according to claim 7, wherein the elongated electrodes are spike electrodes.

10. The implantable electrode array according to claim 7, wherein the elongated electrodes are of varying size.

11. The implantable electrode array according to claim 3, wherein the electrodes are elongated electrodes.

12. The implantable electrode array according to claim 4, wherein the electrodes are elongated electrodes.

13. The implantable electrode array according to claim 5, wherein the electrodes are elongated electrodes.

14. The implantable electrode array according to claim 1, wherein the array body defines a void over the center point.

15. A visual prosthesis comprising:
   a video capture device;
   a video processor receiving video data from the video capture device and converting the video data to stimulation signals;
   an implantable neural stimulator receiving stimulation signals;
   an array body suitable to be implanted adjacent to a retina near its fovea;
   a ring of high density electrodes 3 millimeters or less from a center point of the array; and
   gradually larger and more widely spaced electrodes beyond 3 millimeters from the center point of the array.

16. The visual prosthesis according to claim 15, further comprising an area less than 0.5 millimeter from the center point of the array which contains no electrodes.

17. The visual prosthesis according to claim 15, wherein the electrodes are spaced across the array body at varying intervals and the intervals are smaller toward the center point of the array body and increasing toward an outer edge of the array body proportionately to a distance from the center point.

18. The visual prosthesis according to claim 17, wherein the electrodes are of varying size, and the varying size of the electrodes is small toward the center point of the array body, and increases toward an outer edge of the array body proportionately to a distance from the center point.

* * * * *